United States Patent
Hauge

(10) Patent No.: US 9,119,928 B2
(45) Date of Patent: Sep. 1, 2015

(54) APPARATUS AND METHOD FOR MAINTAINING A SURGICAL AIRWAY

(76) Inventor: Russ Hauge, Woodbury, MN (US)

( * ) Notice: Subject to any disclaimer, the term of this patent is extended or adjusted under 35 U.S.C. 154(b) by 331 days.

(21) Appl. No.: 13/608,093

(22) Filed: Sep. 10, 2012

(65) Prior Publication Data

US 2013/0061854 A1   Mar. 14, 2013

Related U.S. Application Data

(60) Provisional application No. 61/532,146, filed on Sep. 8, 2011.

(51) Int. Cl.
*A61M 16/04* (2006.01)

(52) U.S. Cl.
CPC ....... *A61M 16/0488* (2013.01); *A61M 16/0493* (2014.02); *A61M 16/0497* (2013.01)

(58) Field of Classification Search
CPC .......... A61M 16/049; A61M 16/0493; A61M 16/04; A61M 16/0486; A61M 16/0488; A61M 16/0495; A61M 16/0497
USPC .......... 128/200.26, 207.14–207.17, 859–862; 604/174
See application file for complete search history.

(56) References Cited

U.S. PATENT DOCUMENTS

| | | | | |
|---|---|---|---|---|
| 5,273,032 A | * | 12/1993 | Borody | 128/207.14 |
| 5,413,095 A | * | 5/1995 | Weaver | 128/200.26 |
| 6,257,238 B1 | * | 7/2001 | Meah | 128/859 |
| 7,624,736 B2 | * | 12/2009 | Borody | 128/848 |
| 7,946,288 B2 | * | 5/2011 | Flynn et al. | 128/200.24 |
| 7,975,689 B2 | | 7/2011 | Hauge | |
| 8,555,886 B2 | * | 10/2013 | Colman et al. | 128/207.14 |
| 2007/0068535 A1 | * | 3/2007 | Colman et al. | 128/859 |
| 2010/0101567 A1 | | 4/2010 | Hauge | |
| 2010/0132700 A1 | * | 6/2010 | Filipi et al. | 128/200.26 |

* cited by examiner

*Primary Examiner* — Valerie L Skorupa
(74) *Attorney, Agent, or Firm* — Hamre, Schumann, Mueller & Larson, P.C.

(57) ABSTRACT

An apparatus for maintaining a surgical airway and method for the same includes an elongated body insertable orally into a patient. The elongated body defines leading and trailing ends. A passageway is defined through the leading and trailing ends, such that surgical equipment may be insertable through the opening of the elongated body. A securing member may be connected to the trailing end that can hold the elongated body in a position such that an airway remains open to treat the patient, while supporting oxygen flow to the patient.

9 Claims, 8 Drawing Sheets

APPARATUS AND METHOD FOR MAINTAINING A SURGICAL AIRWAY

This application claims the benefit of U.S. Provisional Application No. 61/532,146 filed on Sep. 8, 2011 and titled APPARATUS AND METHOD FOR MAINTAINING A SURGICAL AIRWAY, the entirety of which is incorporated by reference herewith.

FIELD

The invention relates to an apparatus for maintaining a surgical airway and method of the same. More particularly, an apparatus is disclosed that is to be inserted into and held within a patient's mouth.

BACKGROUND

Devices for maintaining a surgical airway are well known and widely used, such as for enabling a patient to continue breathing during surgical and outpatient procedures. Typically, such devices may be employed in gastro and/or bronchial and/or upper endoscopy surgical procedures, and may be employed in outpatient applications, for instance, where patients experience sleep apnea.

In previous applications, a nasal cannula and bite block combination have been used. However, difficulties arise where a patient does not have a nasal airway or cannot breathe through his/her nose. Employing a nasal cannula and bite block limits the flow of oxygen to a patient. Such devices only deliver 28%-40% oxygen concentration to the patient. Furthermore, the bite block may not be optimally secured, and thus may not always stay in place. Such devices also require extensive modification to be capable of monitoring carbon dioxide.

While these previous applications have provided some advancement for maintaining a surgical airway, improvements may yet be made to such devices. There is a need for improving an apparatus for maintaining a surgical airway that can, for example provide optimal oxygen flow and that has the capability to monitor and detect end tidal carbon dioxide ($ETCO_2$). A device is desirable that can be better secured so as to stay in place, while sufficiently maintaining access to the airway. Improvements may still be made to an apparatus for maintaining a surgical airway that requires less equipment and that can be conveniently used.

SUMMARY

An improved apparatus for maintaining a surgical airway and method for the same is described herein that may overcome difficulties such as described above.

In one embodiment, an apparatus for maintaining a surgical airway and method for the same includes an elongated body insertable orally into a patient. The elongated body defines leading and trailing ends. A passageway is defined through the leading and trailing ends, such that surgical equipment may be insertable through the opening of the elongated body. A securing member may be connected to the trailing end that can hold the elongated body in a position such that an airway remains open to treat the patient, while supporting oxygen flow to the patient.

In one embodiment, an apparatus for maintaining a surgical airway orally through a patient includes an elongated body insertable orally into a patient. The elongated body includes a first end and a second end. One of the first or second ends defines a lead end insertable orally into a patient. The other of the first and second ends defines a trailing end. A flange is disposed at the trailing end, and an opening is disposed at the trailing end allowing access to a passageway through the elongated body between the lead and trailing ends. One or more flow channels are formed within the elongated body and distinct from the opening. The one or more flow channels terminate within the elongated body to define a relatively larger area beyond a termination position of the one or more flow channels. The larger area being larger than a smaller area proximate the opening and disposed adjacent the one or more flow channels.

In one embodiment, an apparatus for maintaining a surgical airway includes at least one securing member support. The securing member support engages the securing member to hold the elongated body in a position such that an airway of the patient remains open.

In one embodiment; an apparatus for maintaining a surgical airway defines at least one aperture therethrough. The aperture(s) enable access to the one or more flow channels. The flow channels are formed within the elongated body and are capable of delivering fluids to the patient and/or monitoring fluid release from the patient, for example delivering supplemented oxygen or monitoring end tidal carbon dioxide.

The apparatus for maintaining a surgical airway provides an improved surgical airway. The apparatus provides a more secure surgical airway that may be disposed after one-time use. The elongated body provides a structure that includes bite block protection and keeps the tongue from obstructing the airway (oral pharynx). The apparatus is capable for monitoring end tidal carbon dioxide release of a patient, so that oxygen may be delivered sooner to the patient. The apparatus also provides supplemental oxygen flow to the patient at a higher concentration and at improved rates without impeding access to the airway.

The apparatus may be employed in various applications requiring maintenance of a surgical airway. Such applications can include but are not limited to esophago-gastro dilatations (EGDs), gastroscopies, bronchoscopies, and upper endoscopy cases. If appropriate, the apparatus may be used in deep monitored anesthesia care (MAC) cases. The apparatus herein can be particularly useful for procedures involving scope placements, intubation, transesophageal echocardiogram (TEE), and dialators. It will be appreciated that the apparatus may be useful for applications that do not require deep sedation, but in appropriate circumstances may be appropriate for applications involving deep sedation. The apparatus further aids in other outpatient procedures, such as those patients suffering from sleep apnea. The apparatus for maintaining a surgical airway requires less equipment for use, for example, no mask is required to cover a patient's face. The apparatus provides an elegant design with improved performance and user convenience.

DETAILED DESCRIPTION OF THE PREFERRED EMBODIMENT

Figure 1:
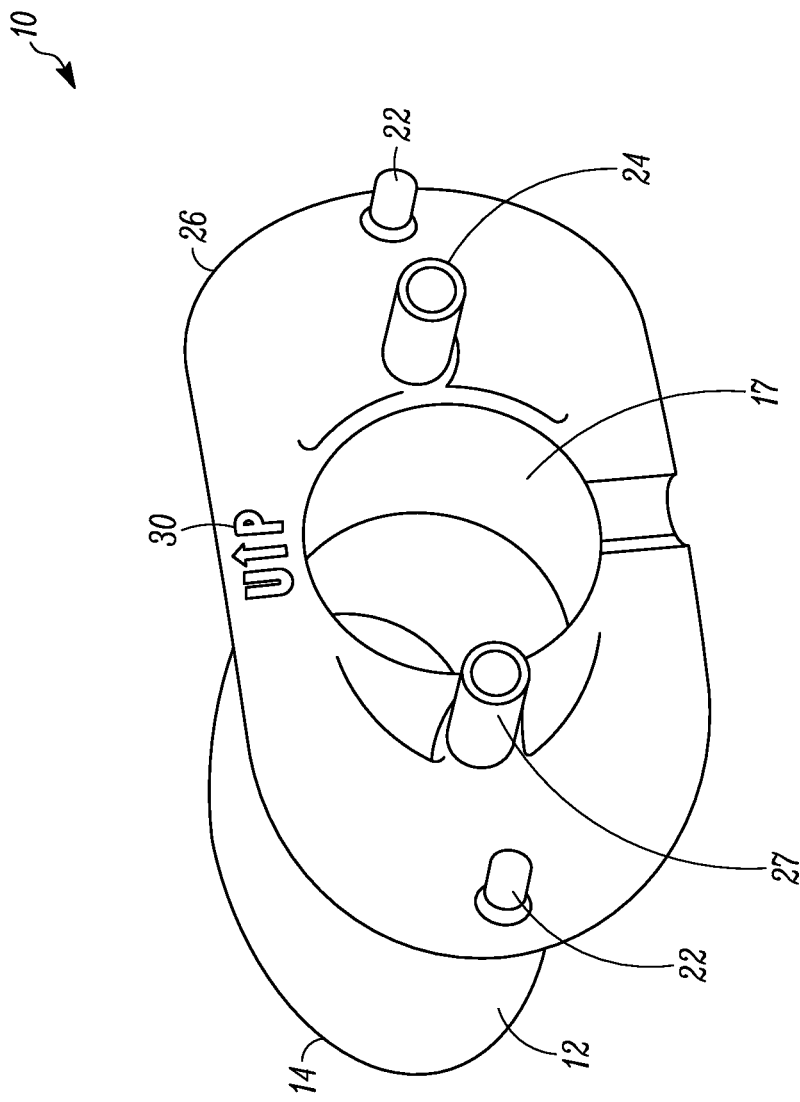
FIG. 1 is a perspective view of one embodiment of an apparatus for maintaining a surgical airway.

One exemplary embodiment of an apparatus 10 for maintaining a surgical airway is shown in FIGS. 1-9.

The apparatus 10 includes an elongated body 12 defining a leading end 14 and a trailing end 16. The elongated body 12 is open through the leading end 14 and the trailing end 16. An opening 17 is disposed at the trailing end 16 for equipment, such as surgical equipment and/or treatment materials to access the inside of the elongated body 12 and be inserted through the leading and trailing ends 14, 16. In some applications, such as in gastro and/or bronchoscope procedures or as in suctioning procedures, the opening 17 enables treatment of the patient through the opening 17 with required medical instruments. The opening 17 provides an airway to be maintained open when the elongated body 12 is inserted orally into the patient. The opening 17 thus can enable insertion of treatment instruments, and can support airflow and oxygen flow to the patient for him/her to breathe.

The elongated body 12 may be constructed of any number of materials, including but not limited to molded softer plastics. In some embodiments, the material may be a latex free clear plastic polymer. It will be appreciated that such materials are exemplary only, as other materials may be equally or more suitable. As one preferred example, the material(s) used to construct the elongated body are medically approved. It will be further appreciated that the elongated body 12 may be limited only to the extent in providing a suitably rigid elongated body structure that does not collapse or cannot be bitten down on while maintaining an open airway of the patient.

Figure 2:
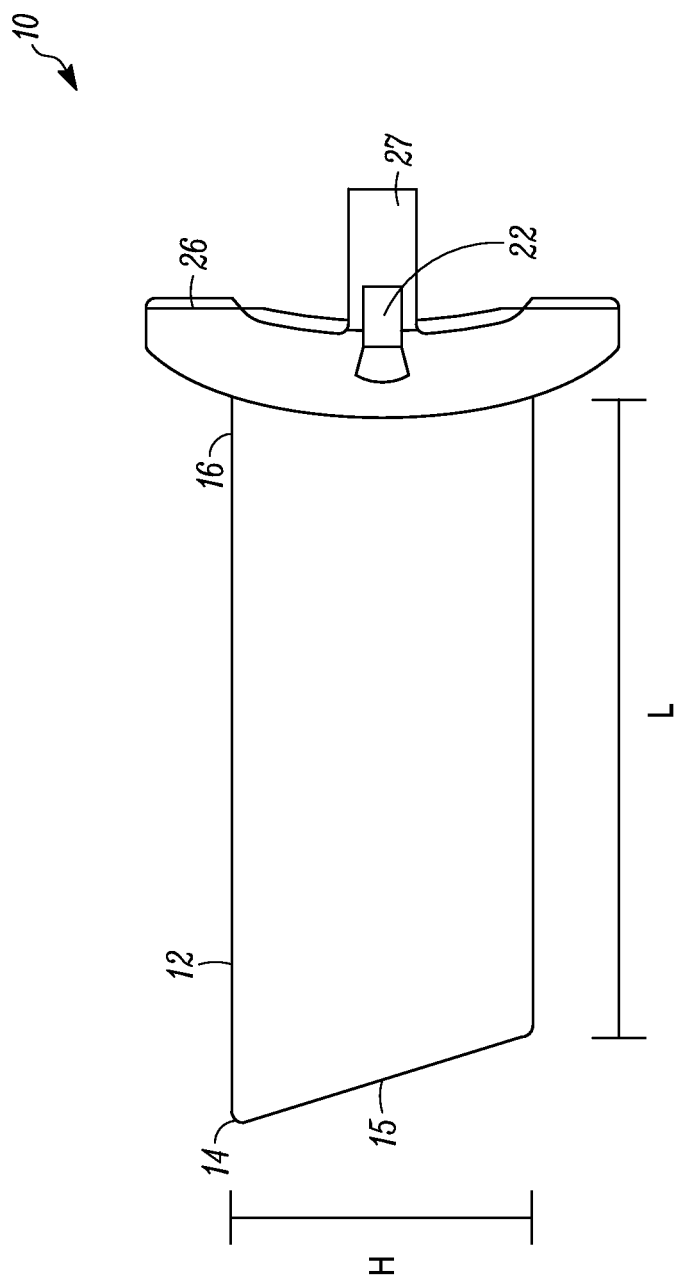
FIG. 2 is a side view of the apparatus of FIG. 1.
Figure 3:
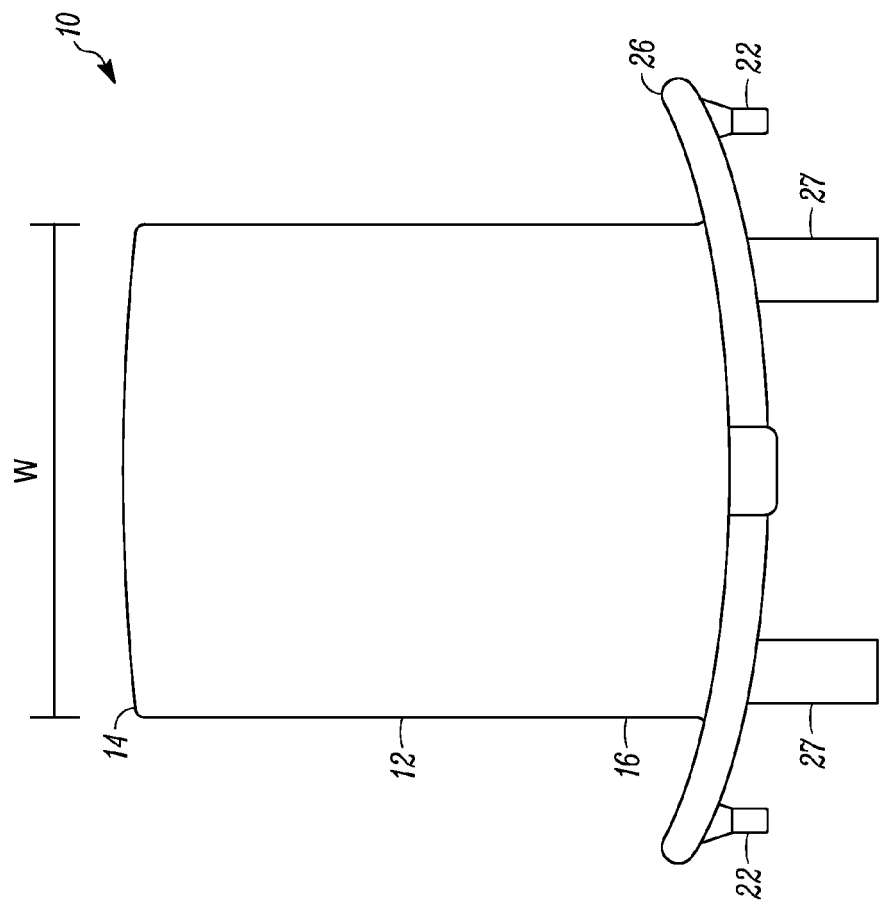
FIG. 3 is a top view of the apparatus of FIG. 1.
Figure 4:
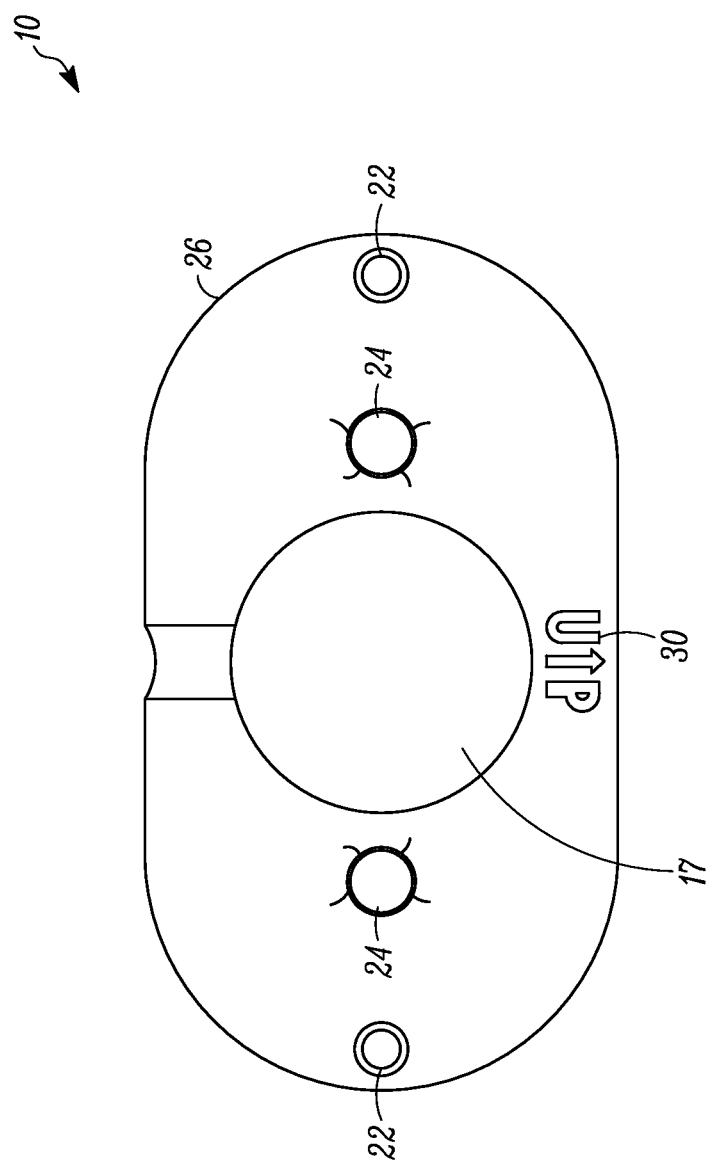
FIG. 4 is a front end view of the apparatus of FIG. 1.
Figure 5:
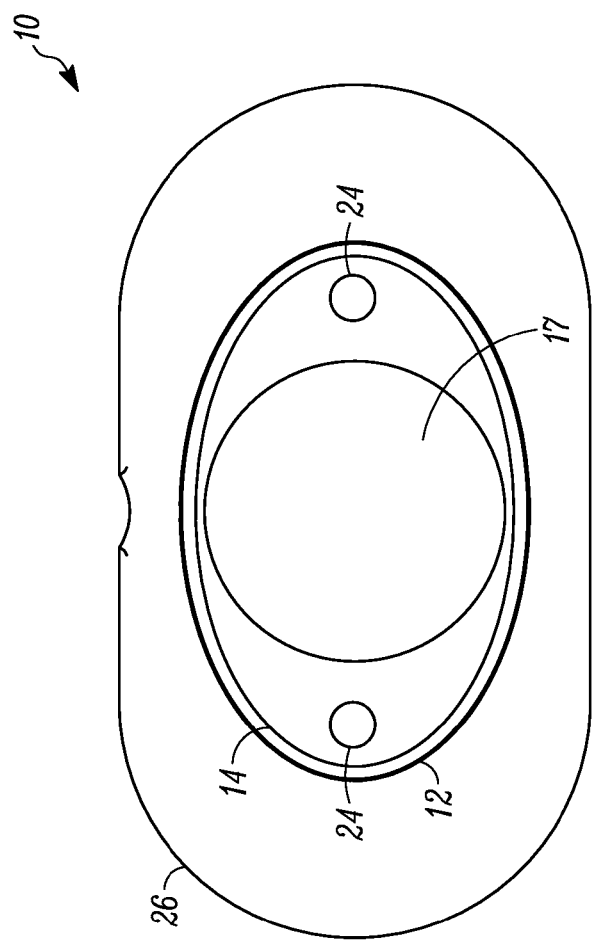
FIG. 5 is a rear end view of the apparatus of FIG. 1.

With further reference to the elongated body 12, in one embodiment the elongated body 12 is relatively straight when viewed from the side and has substantially no curvature along a longitudinal line from the leading end 14 to the trailing end 16 (see e.g. FIG. 2). In another embodiment, the elongated body 12 may have an inward slant portion 15 at the leading end 14 that slants inward from the top toward the bottom. See e.g. FIG. 2. It will be appreciated that there may be no slant 15 at the leading end 14.

Figure 8:
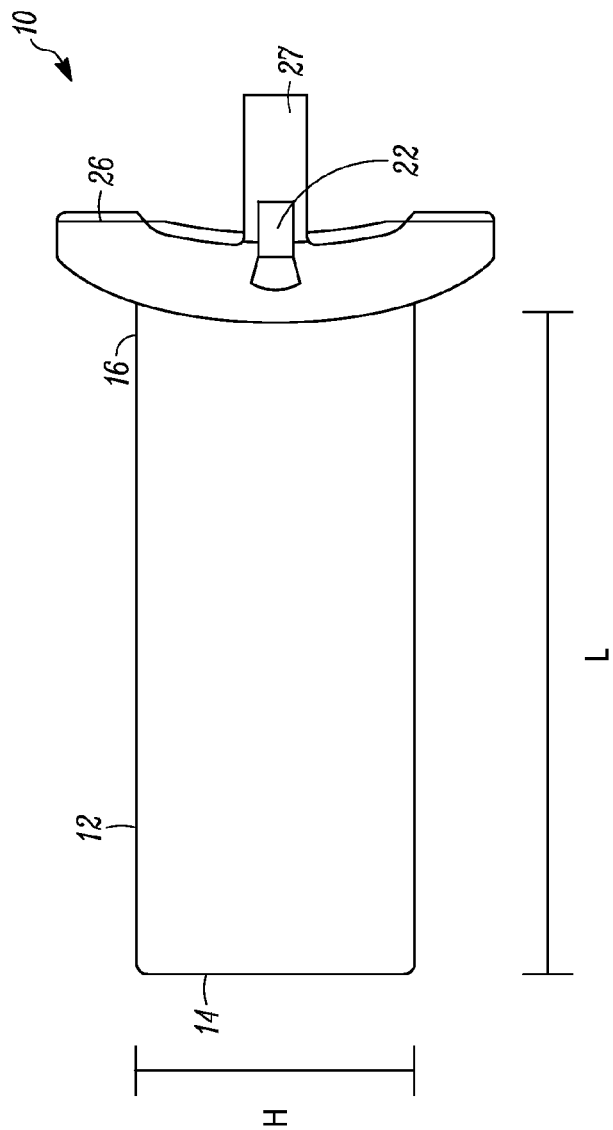
FIG. 8 is a side view of another embodiment of an apparatus for maintaining a surgical airway that is based off FIG. 1.

For example, FIG. 8 shows basically the same apparatus as in FIG. 2, but where there is no inward slant portion 15, and the leading end 14 from top to bottom is generally perpendicular when viewed from the side as in FIG. 8.

As shown, the apparatus 10 includes one or more securing member supports 22 that are disposed proximate the leading end 16. In one embodiment as shown in the drawings, two securing member supports 22 are provided, however it will be appreciated that more or less than two may be employed. In one embodiment, the securing member supports 22 are configured to engage a securing member (not shown) to help secure the apparatus 10 to a patient and can help hold the apparatus 10 in a position so that it can maintain an open airway of the patient.

In one exemplary embodiment, the securing member supports 22 are protrusions or prongs disposed on a flange 26 (further described below), and the securing member supports 22 can extend outward relative to the trailing end 16.

While the securing member is not shown, it will be appreciated that in one embodiment it may be a strap, such as a resilient strap with securing holes that engage the securing member supports. Such straps and their securing holes are shown and described for example in FIGS. 1-5 of U.S. Pat. No. 7,975,689 issued Jul. 12, 2011 and pending U.S. application Ser. No. 12/519,972 filed on Jun. 18, 2009, both of which are incorporated by reference herewith in their entirety. Such straps as shown in the pending applications may be suitably employed as one example of a securing member for apparatus 10 herein. For further description, a securing member may be connected to the trailing end 16, e.g. on the securing member supports 22 at flange 26. The securing member can hold the elongated body 12 in position during use, and can prevent dislodgment of the apparatus 10 from its position. As one exemplary embodiment, the securing member may be a resilient strap with elastic physical characteristics. The securing member may include a plurality of securing holes therethrough and along a side surface of the strap. The securing holes removably attach with a support 22. As one example, opposing ends of the securing member may be removably attached proximate the trailing end 16 of the elongated body 12 by such securing holes. In one embodiment of operation, when the elongated body 12 is inserted orally into a patient, the securing member while it is connected to securing member supports 22 may be dressed around a patient's neck or lower head to secure the apparatus 10. The securing holes of the securing member can enable fine adjustment of the securing member, so as to provide an optimal and comfortable fit for the patient. The securing member can thus stabilize the elongated body 12. It will be appreciated that the securing member may be permanently attached, such as by employing a different strap that is permanently attached but can also be adjusted. The securing member may be constructed of any number of materials, including but not limited to a soft elastic rubber. It will be appreciated that such materials are exemplary only, as other materials may be equally suitable. As one preferred example, the material(s) used to construct the securing member are medically approved. The material employed for constructing the securing member may only be limited by such physical characteristics necessary for securing the elongated body 12 as described, and for providing a comfortable fit around a patient's neck or lower head.

Figure 10:
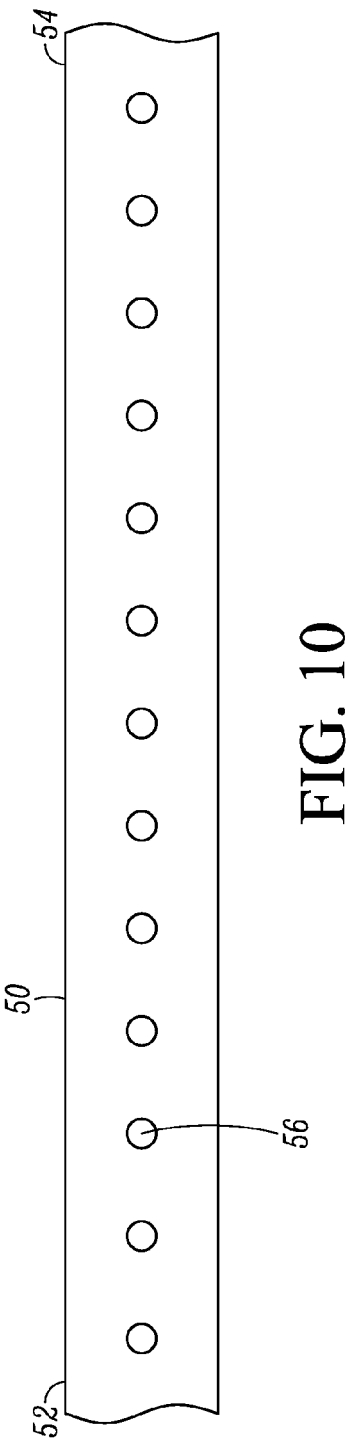
FIG. 10 shows a side diagrammatic view of one embodiment of a securing member.

FIG. 10 shows one embodiment of a securing member 50 that can be a strap with ends 52, 54. The securing member 50 can be wrapped around a patient's head for example, where the supports 22 can be inserted into the securing holes 56.

With further reference to the elongated body 12, in one embodiment the passageway through the elongated body 12 between the leading and trailing ends 14, 16, widens within the elongated body for example at annular shoulder 28. See for example FIGS. 6 and 7. As shown, the passageway through the leading and trailing ends 14, 16 is wider toward and proximate the leading end at area 40 relative to the area 42 toward and proximate the opening 17.

With reference to the flange 26, the flange 26 in one embodiment is disposed proximate the trailing end 16. As shown, the flange 26 may be an oval-like or ellipsoid-like shape that is annularly disposed on the elongated body 12. The flange 26 may provide a face plate structure so as to enable a patient to comfortably fit the apparatus 10 around his/her mouth, while preventing the entire apparatus 10 from being inserted into the patient's mouth. As one example only, the flange 26 can have an arched configuration that is convex facing the trailing end 16 and concave facing the leading end 14. The arched configuration can provide a more comfortable fit of the apparatus 10, where the flange 26 resides external to the patient's mouth and on his/her face. It will be appreciated that the flange 26 is not limited to the specific structure shown and may be suitably modified to achieve the comfortable fit desired, while preventing the entire apparatus from being inserted into a patient's mouth.

Apertures 24 are shown that extend through the flange 26 and into the elongated body 12. The apertures 24 are disposed in outward extending prongs 27 having openings therethrough to access the inside of the elongated body 12. The prong structure 27 can allow for tubings or fitments (not shown) to be attached so as to access the apertures 24. It will be appreciated that such tubings and fitments are known. For example, such tubings and fitments are shown and described for example in FIGS. 1-5 of U.S. Pat. No. 7,975,689 issued Jul. 12, 2011 and pending U.S. application Ser. No. 12/519,972 filed on Jun. 18, 2009, both of which are incorporated by reference herewith in their entirety. Such tubings and fitments may be suitably attached to access the apertures 24. It will be appreciated that the prong structure shown is merely exemplary, and that the apertures are not limited to any specific structure, so long as they enable access to flow channels 44 (described in detail below). In the embodiment shown, the prongs 27 and apertures are disposed between the opening 17 and the securing member supports 22, and the prongs 27 extend outward a distance that is relatively larger than the distance that the securing member supports 22 extend. For example, the prongs 27 have a length that is longer than the securing member supports 22. In one embodiment, prongs 27 an supports 22 extend outward a distance past the opening 17 to allow for easy access to the prongs 27 and 22 relative to the remainder of the apparatus 10.

As mentioned, apertures 24 allow access to the flow channels 44 in the elongated body 12. The apertures 24 extend through the flange 26 to the flow channels 44 inside the elongated body 12. The flow channels 44 are formed within the elongated body 12 as distinct channels separated from the opening 17. A wall structure 46 formed within the elongated body 12 separate the flow channels 44 from the opening 17. In this configuration, the flow channels 44 are formed as a part of the elongated body 12, where the opening 17 and the flow channels 44 provide distinct lumens into the elongated body 12. The flow channels 44 can allow for a more universal apparatus to maintain an airway that is not specific for any particular tubing, and may be adaptable with any desired tubing to attach to the prong structure where the apertures 24 are disposed. As one preferred example, the channels 44 are configured to allow delivery and monitoring of the patient, such as delivering oxygen to the patient and monitoring a patient's $ETCO_2$.

As shown, the flow channels 44 are disposed as two flow channels at opposite sides of the elongated body 12. The flow channels 44 are disposed adjacent the opening 17 and proximate sides of the elongated body 12. It will be appreciated that only one flow channel or more than two flow channels may be formed in the elongated body 12. It further will be appreciated that the flow channels 44 shown are not limited to being positioned at opposite sides or in any specific orientation, so long as they are formed within the elongated body 12.

In one embodiment, the flow channels 44 terminate at annular shoulder 28 where the passageway widens from area 42 to 40. See FIGS. 6 and 7. Such configuration can allow for example, use of the relatively larger area 40 for more efficient and better manipulation of the inserted equipment. That is, the area 40 can be larger than if the channels 44 extended through the elongated body 12 from the leading and trailing ends 14, 16. The termination of the flow channels 44 within the body can help insure better oxygen flow and end tidyl carbon dioxide detection without possible occlusion created by one's tongue, since the elongated body 12 is relatively straight without substantial curve, and since the elongated body 12 is relatively short in the direction of the leading and trailing ends 14, 16.

Figure 6:
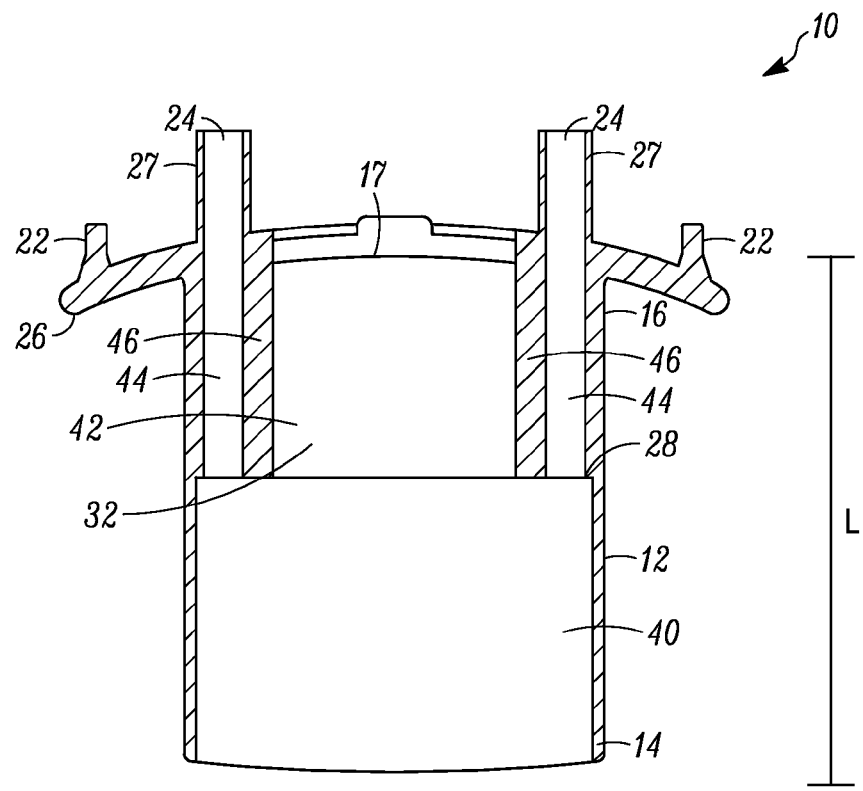
FIG. 6 is a sectional view from the top of the apparatus of FIG. 1.
Figure 7:
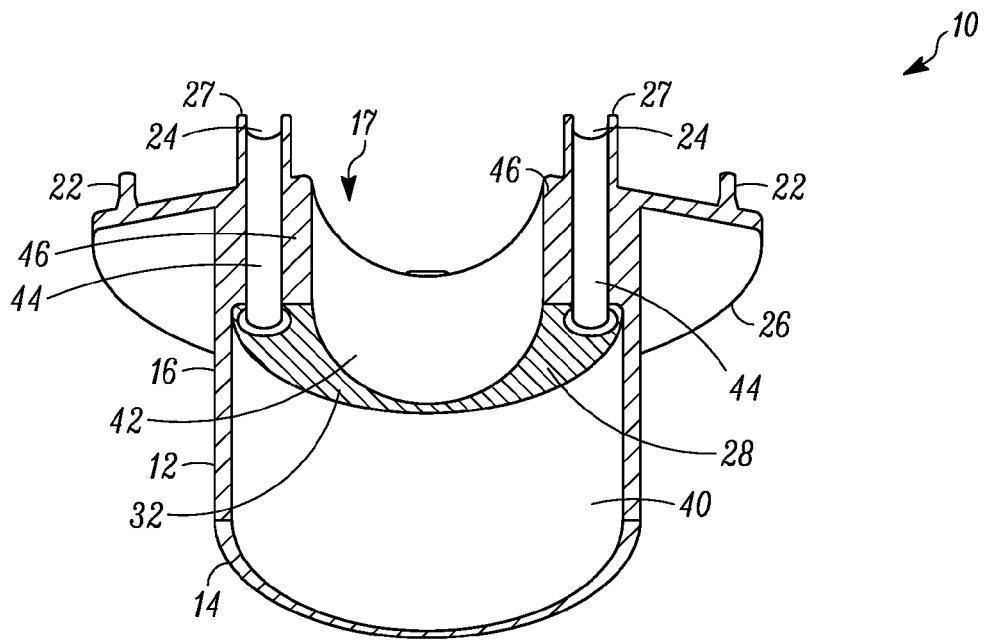
FIG. 7 is another sectional view from rear perspective of the apparatus of FIG. 1.

In FIG. 6, the length dimension from the annular shoulder 28, where the area 42 terminates, to the leading end 14 can be larger than the length dimension from trailing end 16 to the annular shoulder 28. It will be appreciated that the length dimension of area 42 and the length dimension of area 40 (from leading to trailing ends 14, 16) can have the same or similar dimension.

Figure 9:
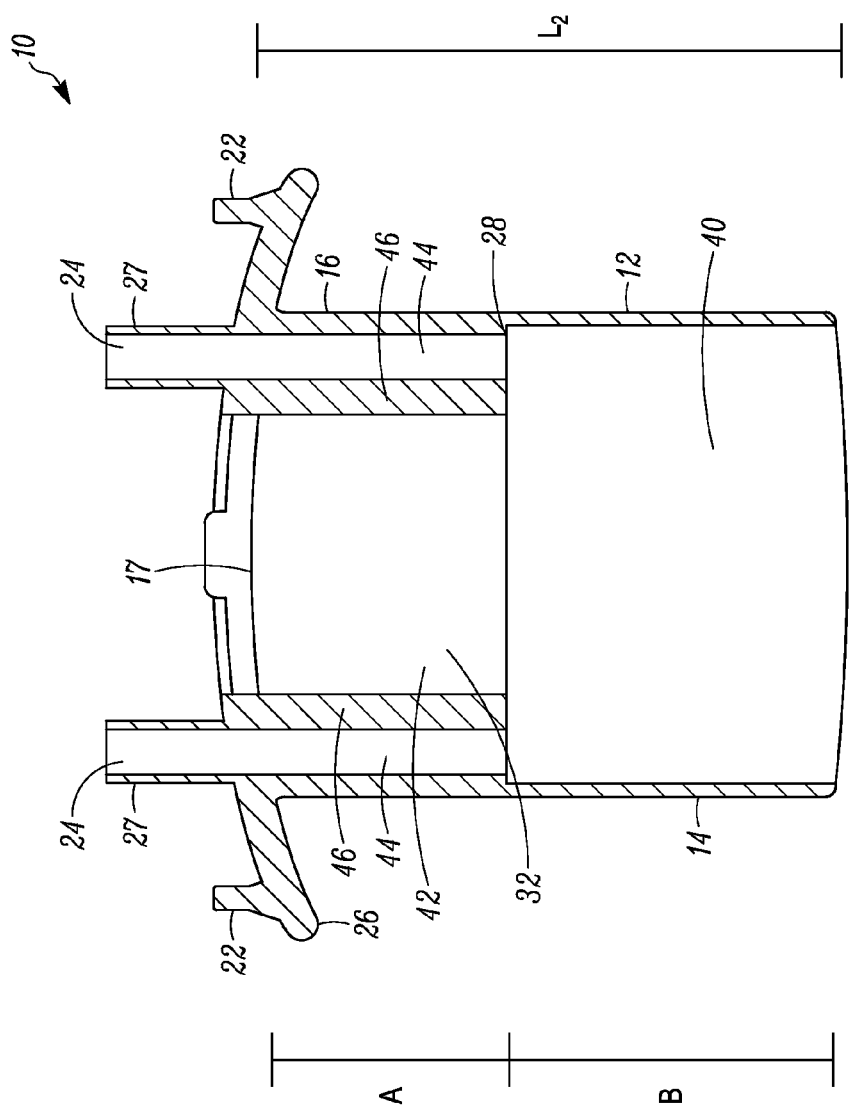
FIG. 9 is a sectional view from the top of the apparatus shown in FIG. 8 and based off FIG. 1.

For example, in FIG. 9, which is basically the same apparatus as shown in FIG. 6, shows a modified length dimension "B" of the wider portion or area 40. Length dimension "B" is defined from the annular shoulder 28 to the leading end 14. As shown in FIG. 9, the length dimension $L_2$ from leading end 14 to trailing end 16 includes length dimensions "B" and "A", where the length dimension "B" is similar to length dimension "A", which is the dimension from trailing end 16 to the annular shoulder 28.

It will also be appreciated that the length dimension "B" could be shorter than the length dimension "A". Thus, the length dimension "B", from the annular shoulder 28 to the leading end 14, can be the same or shorter than the length dimension "A" from the trailing end to the annular shoulder 28.

As one preferred example only, the apparatus 10 may be constructed of an injection molded material that is medically approved, such as but not limited to a medically approved plastic material. The material may be, but is not limited to, an approved polypropylene material. In the configurations shown, the apparatus 10 may be formed such that the elongated body (including the opening and flow channels), the flange, and the extended portion are all constructed as a one-piece unitary structure that is injection molded.

In one embodiment, the elongated body 12 can be reinforced to provide additional bite block protection. For example, the elongated body 12 can be constructed so that it has a thicker portion 32 disposed under the top of the body 12, such as under a horizontal plane about a third of the length from the trailing end 16 toward the leading end 14. The smaller area 42 and wall structure 46 may also provide reinforcement. See side view of FIG. 2 and the sectional views of FIGS. 6 and 7. In some embodiments, an indicator 30 shown in one example as a "U↑P" is used to indicate the correct orientation of the apparatus 10 when inserted in a person's mouth. The indicator 30, for example, shows the "up" placement of the apparatus.

The embodiments described above can provide an improved apparatus for maintaining an open airway with many benefits. For example, the elongated body with its rigid outer structure provides a bite block to prevent a patient from closing his/her mouth and prevents the airway from collapsing. Thus, the bite block function facilitates maintaining the airway in an open position. In conditions where a patient may experience a seizure, for example, the outer structure of the elongated body prevents the opening from collapsing even when a patient bites down on the apparatus. As one preferred example, any of the apparatuses described may be constructed and arranged for one-time use, such as for use on a per patient basis.

Any of the described apparatuses may include a variety of dimensions suitable for both adults and children. As an example for adult sizes, the elongated body 12 may include a length "L" from leading end to trailing end that is approximately 4 inches, sometimes about ⅔ this length, such as for example about 2-3 inches. In one example the length of the elongated body 12 may be approximately 2.5 to 2.6 inches. A width "W" of the elongated body may have a range from approximately 1.0 inches to approximately 2.0 inches and suitable for both males and females. A height "H" or thickness of the elongated body 12 may be approximately 0.75 inches to approximately 1.0 inches. The passageway within the elongated body 12 at area 42 may include a width of approximately 1⅛ inches, whereas the passageway of the elongated body at area 40 is larger and may be approximately 1.75 inches.

It will be appreciated, however, that such dimensions are exemplary only. Other dimensions may be employed that are equally or more suitable to achieve the desired functions of the above embodiments. Thus, the dimensions of any of the described apparatuses, and particularly of the elongated body, are only limited to provide appropriate sizes related to a patient's age and gender, and may be suitably sized as necessary to fit a patient for optimal results.

The embodiments described provide a more secure surgical airway that may be disposed after one-time use. The elongated body provides a structure that includes bite block protection and keeps the tongue from obstructing the airway (oral pharynx). The apparatus is capable for monitoring $ETCO_2$ of a patient. Supplemental oxygen flow may be provided to the patient at a higher concentration and at improved rates, without impeding access to the airway. The apparatus provides that oxygen concentrations may be improved as high as 60-80%. Furthermore, the apparatus for maintaining a surgical airway requires less equipment for its use, for example, no mask is required to cover a patient's face. The apparatus provides an elegant design with improved performance and user convenience.

The apparatus may be employed in known medical procedures, such as but not limited to, gastro and/or bronchial and/or upper endoscopy surgical procedures, and may be employed in outpatient applications, for instance, where patients experience sleep apnea. As some additional examples only, such applications can include but are not limited to esophago-gastro dilatations (EGDs), gastroscopies, bronchoscopies, and upper endoscopy cases. If appropriate, the apparatus may be used in deep monitored anesthesia care (MAC) cases. It will be appreciated that the apparatus may be employed in any number of applications and procedures, and is not limited to those listed. It will be appreciated that any procedure requiring an open airway of a patient to be maintained may employ the apparatus as already described.

The above specification provides a complete description of the composition, manufacture and use of an improved apparatus for maintaining a surgical airway in accordance with the principles of the present invention. Since many embodiments an apparatus for maintaining a surgical airway can be made without departing from the spirit and scope of the invention, the invention resides in the claims hereinafter appended.

The invention claimed is:

1. An apparatus for maintaining a surgical airway orally through a patient, comprising:
    an elongated body insertable orally into a patient, the elongated body including a first end and a second end, one of the first or second ends defining a lead end insertable orally into a patient, the other of the first and second ends defining a trailing end, the elongated body having an axial direction defined between the lead end and the trailing end;
    a flange disposed at the trailing end;
    an opening disposed at the trailing end allowing access to a passageway through the elongated body between the lead and trailing ends;
    two securing member supports extending out of the flange parallel to the axial direction of the elongated body, the two securing member supports being disposed on opposite sides across a diameter of the opening,
    two prongs extending out of the flange parallel to the axial direction of the elongated body, the prongs being disposed radially closer to the opening in relation to the securing member supports, the prongs being linearly aligned with the securing member supports on a direction along the diameter of the opening; and
    two flow channels, each flow channel extending from an end of one prong into the elongated body and terminating at an annular shoulder within the elongated body, the flow channels being parallel to the axial direction of the elongated body, the flow channels defining air flow passages distinct from the opening, the annular shoulder defining a relatively larger area beyond the annular shoulder, the larger area being relatively larger than a smaller area proximate the opening and trailing end to the annular shoulder.

2. The apparatus of claim 1, wherein, from the annular shoulder to the leading end, a length dimension is defined that is longer than a length dimension from the trailing end to the annular shoulder.

3. The apparatus of claim 1, wherein, from the annular shoulder to the leading end, a length dimension is defined that is the same or shorter than a length dimension from the trailing end to the annular shoulder.

4. A method of maintaining a surgical airway orally through a patient, comprising:
    inserting an apparatus as in claim 1;
    creating a surgical airway with the apparatus as in claim 1; and
    maintaining the surgical airway with the apparatus as in claim 1.

5. The apparatus according to claim 1, wherein the elongated body has a length approximately 4 inches from leading end to trailing end.

6. The apparatus according to claim 1, wherein the elongate body has a width ranging from approximately 1 to 2 inches.

7. The apparatus according to claim 1, wherein the elongated body has a height ranging from approximately 0.75 to 1 inches.

8. The apparatus according to claim 1, further comprising a strap securable to the securing member supports to secure the apparatus when inserted orally into the patient.

9. The apparatus according to claim 1, further comprising an indicator indicating a correct orientation of the apparatus when inserted orally into the patient.

* * * * *